United States Patent [19]

Stanley, Jr. et al.

[11] Patent Number: 5,275,935
[45] Date of Patent: Jan. 4, 1994

[54] AMEBIC GLYCOCONJUGATE AND MONOCLONAL ANTIBODY

[75] Inventors: Samuel L. Stanley, Jr.; Ellen Li, both of Ladue, Mo.

[73] Assignee: Washington University, St. Louis, Mo.

[21] Appl. No.: 943,095

[22] Filed: Sep. 10, 1992

[51] Int. Cl.$^5$ ............... G01N 33/569; C07K 15/28; C12P 21/08; C12N 5/12

[52] U.S. Cl. .................. 435/7.22; 530/388.1; 530/388.6; 435/70.21; 435/240.27; 536/1.11

[58] Field of Search ............ 424/88; 530/396, 350, 530/388.1, 388.6; 435/7.22, 28, 320.1, 70.21, 240.27; 536/1.1, 1.11

[56] References Cited

U.S. PATENT DOCUMENTS 5,130,417 7/1992 Stanley et al. .................. 530/350

OTHER PUBLICATIONS

Arroyo et al., Molec. Biochem. Parasitol, 23 (1987) pp. 151-158.
McConville et al., Proc. Natl. Acad. Sci. vol. 84 (1987) pp. 8941-8945.
Stanley, et al., Molec. Biochem. Parasitol, 50 (1992) pp. 127-138.
Petri et al., J. Clin. Invest., 80 (1987), pp. 1238-1244.
Meza et al., J. Inf. Dis., vol. 156, No. 5, (1987), pp. 798-805.
Win Stanley et al., Chapter 119, from vol. 4 Applications of Immunological Methods in Biomedical Sciences, Ed D. M. Weir, Blackwell Scientific Publications, 1986.
Bhattacharya et al., Inf. and Imm., vol. 58, No. 10, pp. 3458-3461, 1990.
Bhattacharya et al., Molec. and Biochem. Parasitol., 56: 161-168, 1992.
Zhang et al., J. Clin. Micro, vol. 30, No. 11, 2788-92, 1992.
Stanley et al., Mol. & Biochem. Parasitology 50, 127-138 (1992).
Li et al., J. Exp. Med. 167, 1725-1730 (1988).
Li et al., Infect. Immunol. 57, 8-12 (1989).
Stanley et al., Proc. Nat'l. Acad. Sci. USA, 87, 4976-4980 (1992).
Ravdin et al., Infect. Immunol. 53, 1-5 (1986).

Primary Examiner—Y. Christina Chan
Assistant Examiner—Ron Schwadron
Attorney, Agent, or Firm—Scott J. Meyer

[57] ABSTRACT

An amebic glycoconjugate is disclosed that is recognized by an *Entamoeba histolytica* specific monoclonal antibody The glycoconjugate is isolated from the lysates of *E. histolytica* trophozoites, it is phosphorylated, lipid-containing, glycosylated, migrates as a polydisperse band on SDS-PAGE between about 65-200 kDa and is specifically recognized by monoclonal antibody CC 8.6, ATCC HB 11104.

3 Claims, 9 Drawing Sheets

AMEBIC GLYCOCONJUGATE AND MONOCLONAL ANTIBODY

BACKGROUND OF THE INVENTION

This invention relates to a novel amebic glycoconjugate that is recognized by an *Entamoeba histolyica* specific monoclonal antibody.

The protozoan pathogen *Entamoeba histolytica* is a major cause of debilitating illness and death worldwide, infecting more than 500,000,000 people, and causing an estimated 50,000,000 cases of diarrhea, and 50,000 deaths yearly [Walsh in *Amebiasis, Human Infection by Entamoeba histolytica*, ed. Ravdin, J. I., John Wiley & Sons, Inc. New York, NY, pp. 93-105 (1988).

The ability of the protozoan parasite *Entamoeba histolytica* to adhere to target cells appears to be a critical component for pathogenesis. Studies of axenically cultured *E. histolytica* interacting with mammalian cell lines have shown that target cells in direct contact with trophozoites show extensive blebbing, morphologic changes, and trypan blue uptake, while neighboring cells not in direct contact remain intact [1]. The importance of adhesion in the pathogenesis of *E. histolytica* disease emphasizes the need for isolating surface molecules that may play a role in this critical function.

BRIEF DESCRIPTION OF THE INVENTION

In accordance with the present invention a novel amebic glycoconjugate is provided which is recognized by an *Entamoeba histolytica* specific monoclonal antibody. This unique amebic glycoconjugate is expressed on the surface of the *E. histolytica* trophozoite; it is a phosphorylated, lipid-containing glycoconjugate. Antibodies to this antigenic glycoconjugate have the biological property to protect against *E. histolytica* adhesion and cytotoxicity.

To study surface molecules of *E. histolytica*, monoclonal antibodies were produced from mice immunized with lysate from the pathogenic amebic strain HM1:IMSS, and screened for the ability to inhibit *E. histolytica* adhesion. One monoclonal antibody, CC 8.6, was a potent inhibitor of amebic adhesion to a Chinese hamster ovary cell line, and was capable of inhibiting HM1:IMSS mediated cytotoxicity by 50%. It was found that monoclonal antibody CC 8.6 bound to a novel amebic glycoconjugate. As shown by ELISA and Western blotting data using monoclonal antibody CC 8.6, the glycoconjugate is present only in *E. histolytica* and not in other Entamoeba sp. It migrates as a polydisperse band on SDS-PAGE between about 65 to 200 kDa, and can be metabolically radiolabeled with [$^{14}$C] glucose, [$^{32}$P]phosphate, and [$^{3}$H]palmitate. The glycoconjugate can be purified by hydrophobic interaction chromatography on octyl-Sepharose; enzymatic hydrolysis with phosphatidylinositol-specific C alters the hydrophobic properties of the molecule. HPLC analysis of [$^{14}$C]glucose-labeled glycoconjugate saccharides revealed that approximately 82% of the incorporated label was in glucose and 12% in galactose.

Among 27 monoclonal antibodies which specifically bound to HM1:IMSS, CC 8.6 was the only monoclonal antibody isolated that could inhibit amebic mediated cytolysis of target CHO cells. An isolate of the hybridoma cells for production of monoclonal antibody CC 8.6 is on deposit with the American Type culture collection 12301 Parklawn Drive, Rockville, Maryland under accession number ATCC HB 11104 said deposit was made on Aug. 25, 1992.

The ability of monoclonal antibody CC 8.6 which binds the glycoconjugate to specifically recognize *E. histolytica* strains indicated that this molecule also is useful as a diagnostic reagent.

The inhibitory activity exhibited by monoclonal antibody CC 8.6 in in vitro adhesion and cytotoxicity assays, also indicates that the amebic glycoconjugate can play a role in the pathogenesis of *E. histolytica* infection, and can be useful in vaccine development.

DETAILED DESCRIPTION OF THE INVENTION

While the specification concludes with claims particularly pointing out and distinctly claiming the subject mater regarded as forming the present invention, it is believed that the invention will be better understood from the following detailed description of preferred embodiments taken in conjunction with the accompanying drawings, in which:

BRIEF DESCRIPTION OF THE DRAWINGS

FIG. 2 shows the detection of the antigen recognized by monoclonal antibody CC 8.6 in *Entamoeba sp.* by Western blotting. Lane 1, HM1:IMSS lysates; lane 2, CC 8.6 immunoprecipitated HM1:IMSS lysates; lane 3, Laredo lysates; lane 4, *E. invadens* lysates; lane 5, *E. moshkoyskii* lysates; lane 6, *E. histolytica* 200:NIH:lysates; lane 7, *E. histolytica* Rahman lysates.

FIG. 3 shows in two parts, FIG. 3A and FIG. 3B, the isolation of amebic glycoconjugate from [$^{14}$C]glucose-labeled HM1:IMSS trophozoites. Panel (A). Lane 1, 20 µl of resuspended pellet from lysates of [$^{14}$C]glucose-labeled HM1:IMSS; lane 2, 20 µl of supernatant from lysates of [$^{14}$C]glucose-labeled HM1:IMSS; lane 3, HPCµ2 immunoprecipitated material from 1 ml of supernatant from lysates of [$^{14}$C]glucose labeled HM1:IMSS; lane 4, CC 8.6 immunoprecipitated material from 1 ml of supernatant from lysates of [$^{14}$C]glucose-labeled HM1:IMSS. Panel (B). Lane 1, 20 µl of the water saturated with 1-butanol extract of delipidated HM1:IMSS trophozoites (metabolically labeled with [$^{14}$C]glucose) in 0.5M TES/5% 1-propanol; lane 2, 20 µl of fraction 16 from OCTYL SEPHAROSE affinity chromatography Resin fractionation; lane 3, 20 µl of fraction 59 (CC 8.6 immunoreactive) from octyl-Sepharose fractionation.

FIG. 4 shows that the amebic glycoconjugate incorporates [$^{3}$H]palmitate. Lane 1, 20 µl of resuspended pellet from lysates of [$^{3}$H]palmitate-labeled HM1:IMSS; lane 2, 20 µl of supernatant from lysates of [$^{3}$H]palmitate-labeled HM1:IMSS; lane 3, CC 8.6 immunoprecipitated material from 1 ml of supernatant from lysates of [$^3$H]palmitate-labeled HM1:IMSS; lane 4, HPCμ2 immunoprecipitated material from 1 ml of supernatant from lysates of [$^3$H]palmitate-labeled HM1:IMSS.

FIG. 5 shows that the amebic glycoconjugate incorporates [$^{32}$P]phoshate. Lane 1, CC 8.6 immunoprecipitated material from 1 ml of supernatant from lysates of [$^{32}$P]phosphate-labeled HM1:IMSS; lane 2, 20 μl of supernatant from lysates of [$^{32}$P]phosphate-labeled HM1:IMSS; lane 3, 20 μl of resuspended pellet from lysates [$^{32}$P]phosphate-labelled of HM1:IMSS

FIG. 7 shows in two parts, FIG. 7A and FIG. 7B, the HPLC analysis of the acid hydrolysate of [$^{14}$C]glucose-labeled glycoconjugate on a borate anion column.

The production of monoclonal antibodies having the characteristics of CC 8.6 as described herein can be carried out by conventional procedures such as described, for example, by Kohler and Milstein, *Nature* 256, 495–497 (1975); *Eur. J. Immunol.* 6, 511–519 (1976). According to this method, tissue-culture adapted mouse myeloma cells are fused to spleen cells from immunized mice to obtain the hybrid cells that produce large amounts of a single antibody molecule. In this procedure a preparation of *E. histolytica* trophozoites was used as the immunogen. This protein antigen is sufficiently large so that no hapten is necessary for immunogenicity.

A suitable mouse myeloma cell line for use in making these antibodies is the Sp2/o-Ag14 cell line. This is a well-known cell line of BALB/c origin defined by Schulman, Wilde and Köhler, *Nature* 276, 269–270 (1978). These cells, which do not synthesize Ig chains, can be obtained from the Basel Institute for Immunology and are available to the public from the American Type Culture Collection, Rockville, MD., under accession number ATCC CRL-1581. A preferred mouse myeloma cell line which also is a non-secretor cell line of BALB/c origin is P3-X63-Ag8.653 [Kearney et al., *J. Immunol.* 123, 1548–1550 (1979)]. A preferred method of carrying out the fusion of the myeloma cells and the spleen cells is by the conventional general procedure described by Galfre et al., *Nature* 266, 550–552 (1977). This method employs polyethylene glycol (PEG) as the fusing agent for the cells growing as monolayers, followed be selection in HAT medium (hypoxanthine, aminopterin and thymidine) as described by Littlefield, *Science* 145, 709–710 (1964).

Further background information on suitable methodology for producing monoclonal antibodies can be had by reference to common texts in the field, for example, Goding, "Monoclonal Antibodies: Principles and Practice", Academic Press, NY., 1983.

It will be appreciated that not all hybridomas prepared as described herein will have optimum antibody activity. As is customary in this field, radioimmunoassay and enzyme immunoassay procedured can be readily used to screen the population of hybridomas for individual clones which secrete optimum specificity. The radioimmunoassay is based upon the competition between radiolabeled and unlabeled antigen for a given amount of antibody which can be determined by conventional general procedure as described, for example, by Yalow et al. *J. Clin. Invest.* 39, 1557 (1960). In the enzyme immunoassay such as ELISA, the revealing agent is conjugated with an enzyme instead of $^{125}$I. After washing away any unbound material, the bound enzyme is revealed by addition of a substrate which undergoes a color change. See, e.g., Engvall and Perlmann, *Immunochemistry* 8, 871–874 (1971); *J. Immunol.* 109, 129–135 (1972).

The following detailed Example will further illustrate the invention although it will be appreciated that the invention is not limited to this specific Example or the specific details presented therein. In this Example, detailed test procedures were carried out to provide the data and results shown in the accompanying FIGS. 1–8 and in Table I, below, with respect to the novel and unique monoclonal antibody CC 8.6.

EXAMPLE

Materials and Methods

*Cells. E. histolytica* HM1:IMSS, HK-9, 200:NIH, and Rahman, were all obtained from the American Type Culture Collection (ATCC), Rockville, MD. *Entamoeba invadens, Entamoeba moshkovskii,* and the *E. histolytica*-like Laredo strain were also obtained from the ATCC. All amoeba were grown in conventional TYI-33 media as previously described [2]. All *E. histolytica* species were grown at 35° C., while *E. invadens, E. moshkovskii,* and the Laredo strain, were grown at 25° C.

The lectin resistant CHO cell line 1021 was provided by Dr. Stuart Kornfeld and grown as described previously [3].

*Antigen preparation and immunizations. E. histolytica* lysates were used to immunize BALB/c mice. 2×10$^6$ *E. histolytica* HM1:IMSS trophozoites were harvested by chilling 48 hour cultures followed by low speed centrifugation. The trophozoites were washed three times with phosphate buffered saline (PBS) and suspended in 1 ml of PBS. The trophozoites were lysed by sonication (three ten second bursts). The homogenate was centrifuged at 1100×g for 30 minutes at 4° C., and the pellet was discarded. 100 μl of the *E. histolytica* lysate combined with 100 μl of complete Freund's adjuvant was used to immunize each mouse. Mice received two additional boosts with 80 μl *E. histolytica* lysate and 80 μl incomplete Freund's adjuvant at weeks 2 and 6, and received 15 μl of soluble antigen intravenously on week 8, 3 days before fusion. An identical protocol was used to prepare lysates from all other ameba species tested.

*Monoclonal antibodies.* Monoclonal antibodies were prepared using previously described conventional methods of Köhler and Milstein [4]. Antibodies were screened using an enzyme-linked immunoabsorbent assay (ELISA) against *E. histolytica* lysates, and underwent a second screening against bovine serum albumin (BSA), and Laredo lysates. The monoclonal antibody CC8.6 was isotyped by conventional methods as previously described [5]. The origin and characteristics of monoclonal antibodies HPCμ2 (murine IgM, κ-phosphorylcholine binding antibody), M58.6, and 187.1 have been described [5]. Both M58.6 and 187.1 were coupled to alkaline phosphatase as previously described [6]. ELISA's were performed according to the conventional protocol in [5] using a 10 μg ml$^{-1}$ solution of the target antigen in PBS. For immunoprecipitation studies monoclonal antibodies CC8.6, and HPCμ2 were coupled to AFFI-GEL affinity chromatography beads (Bio-Rad, Richmond, CA) using the manufacturers published protocol with the product.

Adherence of [$^3$H]thymidine-labeled *E. histolytica* trophozoites to monolayers of CHO 1021 cells. These tests were performed as described in [7], except varying concentrations of monoclonal antibody CC8.6, media alone, or control monoclonal antibody HPCμ2 were added to the monolayers after the addition of the labeled trophozoites. Subsequent steps were performed as previously described [7].

*Ameba-mediated cytotoxicity assays.* These assays were performed as described in [8], except varying concentrations of monoclonal antibody CC 8.6, media alone, or control monoclonal antibody HPCμ2 were added to the monolayers of [$^{51}$Cr]chromium-labeled CHO 1021 cells immediately before the addition of the trophozoites. $1 \times 10^5$ HM1:IMSS trophozoites were added to each monolayer, and cytotoxicity was measured at two hours. Subsequent steps were performed as previously described [8].

Western blotting. Western blotting of trophozoite lysates was performed using CC 8.6 ascites diluted 1:1000 in blocking buffer with [$^{125}$I]iodine labeled 187.1 (rat anti-mouse κ) as the secondary antibody using the protocol described in [9]. The same protocol was utilized for dot immunoblots.

In vivo labeling. For labeling tests a standard protocol was used. The standard media of 48 hr cultures of ameba, containing $4 \times 10^6$ trophozoites, was replaced with 1 ml of appropriately modified labeling media (α-minimal essential medium containing 0.5% heat inactivated bovine serum, 0.5% BSA, and 5.7 mM cysteine), and the label to be tested. Cultures were incubated for 4 hours at 35° C. then processed as described below. For glucose labeling, 250 μCi [U-$^{14}$C]glucose 2 mCi mmol$^{-1}$ (American Radiolabeled Chemicals Inc. (ARC), St. Louis, MO) was added to 1 ml of glucose-free labeling medium (glucose free α-minimal essential medium (α-MEM) containing 0.5% heat inactivated bovine serum, 0.5% BSA, 5 mM sodium pyruvate, and 5.7 mM cysteine). For phosphate labeling 250 μCi of carrier free [$^{32}$P]phosphate (Amersham, Arlington Heights, IL) was added to phosphate-free labeling medium (phosphate free α-MEM media containing 0.5% heat inactivated bovine serum, 0.5% BSA, and 5.7 mM cysteine). For palmitate labeling, 1 mCi of [9,10-$^3$H]palmitate (NEN, Boston, MA) was added to α-MEM media containing 1 mg ml$^{-1}$ defatted BSA (Sigma, St. Louis, MO), and 5.7 mM cysteine, and incubated 4 hr at 35° C.

The labeled trophozoites were harvested, and washed 3 times in PBS. Pellets were lysed by vortexing for 1 minute in a lysis buffer of 1.2 ml 0.02M Tris-phosphate/0.14M sodium chloride/0.005M EDTA/0.002M benzamidine/0.001M phenylmethylsulfonyl fluoride (PMSF)/1% Triton X-100/1% deoxycholate/10% BSA/0.02% sodium azide, then spun at 10,000 x g at 4° C. for 10 minutes. The supernatants were used immediately for immunoprecipitation as described below.

Immunoprecipitation. 1 ml of trophozoite lysate supernatant was added to 50 μl antibody coupled (CC8.6 or HPCμ2) AFFI-GEL affinity chromatography beads. The mixture was incubated at 4° C. with end over end mixing for 20 hours. The supernatant was removed, and the beads washed 2 times in lysis buffer, 2 times in 0.5M NaCl/0.1M NaHCO$_3$, and 1 time in 0.1M sodium phosphate/0.001M benzamidine/0.0005M PMSF/0.001M EDTA. The beads were boiled in 50 μl of SDS-PAGE sample buffer containing 2-mercaptoethanol. Samples were analyzed using 10% and 12.5% acrylamide gels. For analysis of $^3$H- and $^{14}$C-labeled immunoprecipitates, the gels were soaked in EN$^3$HANCE (NEN, Boston, MA), dried, and exposed to Kodak XAR film (Eastman Kodak, Rochester NY) at −70° C. Prestained molecular weight standards (Amersham, Arlington Heights, IL) were used for each gel.

OCTYL-SEPHAROSE chromatography. 72 hr cultures of HM1:IMSS trophozoites ($28 \times 10^6$) were labeled with 750 μCi [U-$^{14}$C]glucose under the conditions described above, harvested, washed 2 times in 50 mM sodium phosphate buffer/0.17 M NaCl, pH 7.3, and then extracted with 20 vol of chloroform/methanol/water (4:8:3, vol/vol/vol) [10]. The delipidated residue was extracted twice with water saturated with 1-butanol with continuous stirring for 18 hr at 4° C. [11], then insoluble material removed by centrifugation (10,000 x g, 30 min) [12]. The supernatants were lyophilized and washed with chloroform/methanol (2:1 vol/vol) [12]. The residue was dissolved in 0.1 M N-tris(hydroxymethyl)methyl-2-aminoethanesulfonate (Tes) buffer, pH 7.0, containing 5% (vol/vol) 1-propanol and loaded onto an equilibrated OCTYL-SEPHAROSE affinity chromatography Resin (Pharmacia) column at 4 ml hr$^{-1}$ [12]. The column was eluted by addition of a linear gradient of 0.1M Tes buffer containing 5% to 65% 1-propanol with 3 ml fractions collected. The radioactivity of each fraction was determined by counting 20 μl in 10 ml SCINTIVERSE RADIOACTIVITY COUNTER (Fisher Scientific, Pittsburgh, PA). Immunoreactivity with CC 8.6 was determined by spotting 2 μl of a fraction on nitrocellulose paper and immunoblotting with CC 8.6 as described above.

Phosphatidylinositol phospholipase C hydrolysis Purified [$^{14}$C]glucose-labeled glycoconjugate (80,000 cpm) was incubated with 2 units phosphatidylinositol-specific phospholipase C (PI-PLC) derived from culture supernatants of *Bacillus subtilus* transfected with the PI-PLC gene from *B. thuringensis* [13] (provided by Dr. Martin Low, Columbia University) in 25 mM HEPES, pH 7.4, at 37° C. for 2 hr. Cleavage of the hydrophobic moiety was determined by passing the sample through the OCTYL-SEPHAROSE column as described above, and measuring the label in bound and unbound fractions by liquid scintillation spectrometry [12].

Carbohydrate analysis. The [$^{14}$C]glucose-labeled fraction obtained from OCTYL-SEPHAROSE chromatography (fraction 59) was hydrolyzed in 2 N trifluoracetic acid for 2 hr at 100° C. The trifluoracetic acid was removed by evaporation at reduced pressure. The acid hydrolysate was analyzed directly by borate anion exchange HPLC to identify labeled aldoses as described by Barr and Nordin [14]. Alternatively, the acid hydrolysate was reduced with sodium borohydride, N-acetylated, and deionized on a mixed bed resin (AMBERLITE MB-3) prior to analysis on a borate anion exchange column to identify the labeled alditols [14]. [$^{14}$C]aldoses and alditols were detected by monitoring the HPLC effluent mixed RPI 3a70 liquid scintillation cocktail using a Berthold HPLC radioactivity monitor.

Pronase digestion. A 100 μl aliquot of the [$^{14}$C]glucose-labeled fraction obtained from OCTYL-SEPHAROSE chromatography (fraction 59) was incubated with an equal vol. of 1 mg ml$^{-1}$ pronase from *Streptomyces griseus* (Sigma) in PBS or with an equal vol. of PBS alone for 8 hr. at 37° C. [15]. Enzyme treatment was terminated by heating at 100° C. for 5 min. After treatment 20 μl of each sample was added to an equal volume of 2X SDS-PAGE sample buffer containing 2-mercaptoethanol and run on 10% SDS-PAGE and autoradiographed as described above.

RESULTS

Isolation of monoclonal antibody CC 8.6. An ELISA was used to screen 5 separate mouse fusions (2400 hybridomas) and 27 clones were isolated with anti-HM1:IMSS activity, but no reactivity with the Laredo strain or BSA. Positive clones were screened for inhibition of HM1:IMSS adhesion. Monoclonal antibody, CC8.6, which produced an IgM, κ, antibody, inhibited amebic adhesion to target cells (vide infra), and was selected for further analysis.

Monoclonal antibody CC 8.6 inhibits HM1:IMSS trophozoite adhesion and cytotoxicity. The ability of monoclonal antibody CC8.6 to inhibit the adhesion of [$^{3}$H]thymidine-labeled HM1:IMSS trophozoites to monolayers of the 1021 CHO cell line was examined. It was found that CC8.6, was a potent inhibitor of amebic adhesion, reducing adhesion to 2% ±2% of control values (media alone) (Table 1). Equivalent concentrations of the isotype and allotype matched control antibody HPCμ2 showed a moderate effect, reducing adhesion to 81% ±4% of the values seen with a media control. The difference between the inhibitory effect of CC 8.6 and the control antibody was significant at the p<0.005 level. Monoclonal antibody CC 8.6 was also capable of inhibiting HM1:IMSS mediated cytotoxicity. CC 8.6 reduced the HM1:IMSS mediated cytolysis of chromium labeled 1021 cell lines to 45% ±11% of control levels (Table I). The control monoclonal antibody, HPC2 reduced cytolysis to 83% ±5% of the values seen with the media control. The difference between the inhibitory effect of CC 8.6 and the control antibody was significant at the p<0.025 level.

Figure 1:
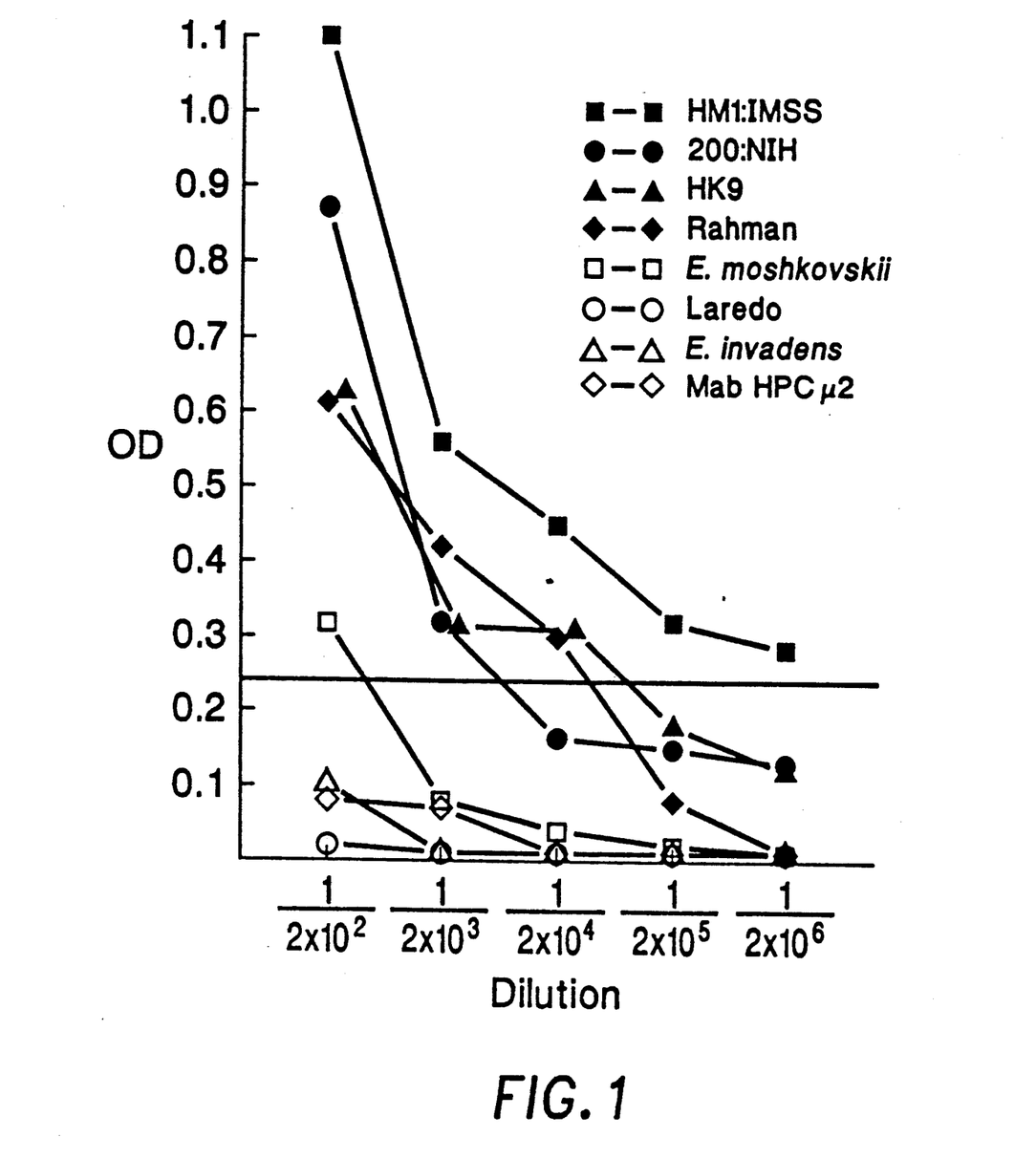
FIG. 1 is a graphical representation which shows the expression of the antigen recognized by monoclonal antibody CC 8.6 on *Entamoeba sp.* measured by ELISA. Monoclonal antibody CC 8.6 as ascites was titrated as shown and reacted with lysates from *E. histolytica* strains: HM1:IMSS, 200:NIH, HK9, and Rahman; and *E. moshkovskii*, Laredo, and *E. invadens*. Binding of ascites from the control monoclonal antibody HPCµ2 to HM1:IMSS was also measured. The absorbance (A) was measured at 410 nm and a background value of 0.240 was subtracted from each measurement. A line is drawn at 0.240 which represents 2×background, so all values above this line were taken as significant above background level.
Figure 2:
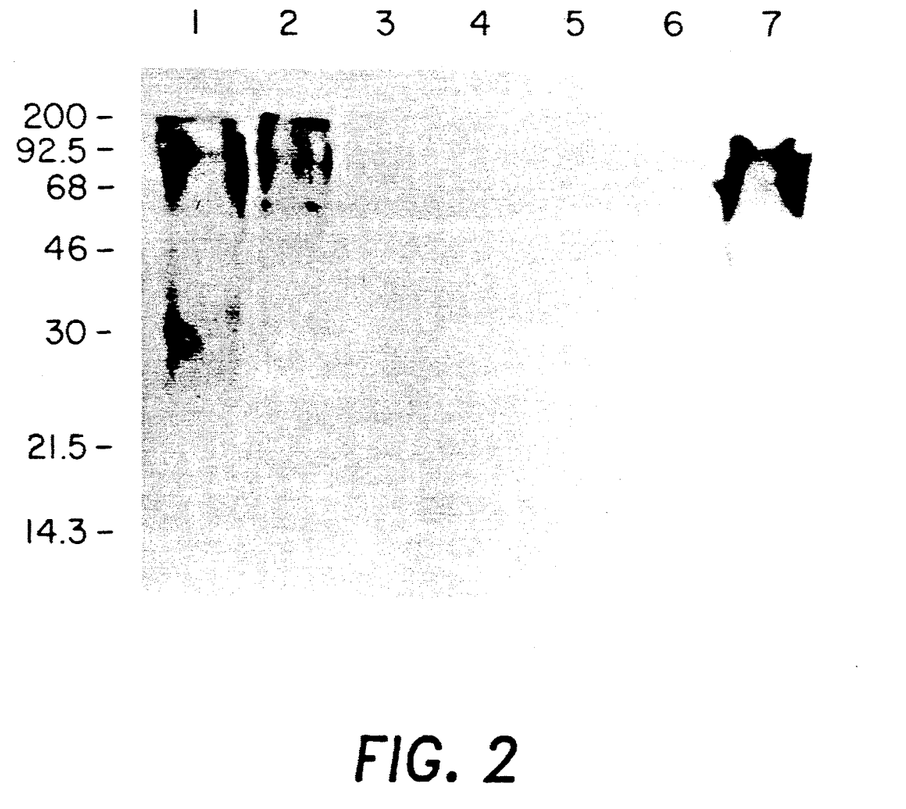

The antigen bound by monoclonal antibody CC 8.6 is found only in strains of *E. histolytica*. It was found that monoclonal antibody CC8.6 bound only to lysates from *E. histolytica* strains (FIG. 1). By ELISA, CC8.6 ascites bound to HM1:IMSS, and to a lesser extent to the *E. histolytica* strains HK9, Rahman, and 200:NIH. It did not show significant binding to the *E. histolytica*-like Laredo strain, *E. invadens*, or *E. moshkoyskii*. Ascites from the isotype and allotype matched control monoclonal antibody, HPCμ2, showed no binding to any of the tested lysates at any of the dilutions. The results of the ELISA were confirmed by Western blot analysis (FIG. 2). Monoclonal antibody CC 8.6 recognized a poly-disperse band, corresponding to a region of the gel spanning molecular weight standards of 65 to 200 kDa in lysates from HM1:IMSS, HK9, Rahman, and 200:NIH. No reactivity with lysates from Laredo, *E. invadens*, or *E. moshkoyskii* was seen.

Figure 3A:
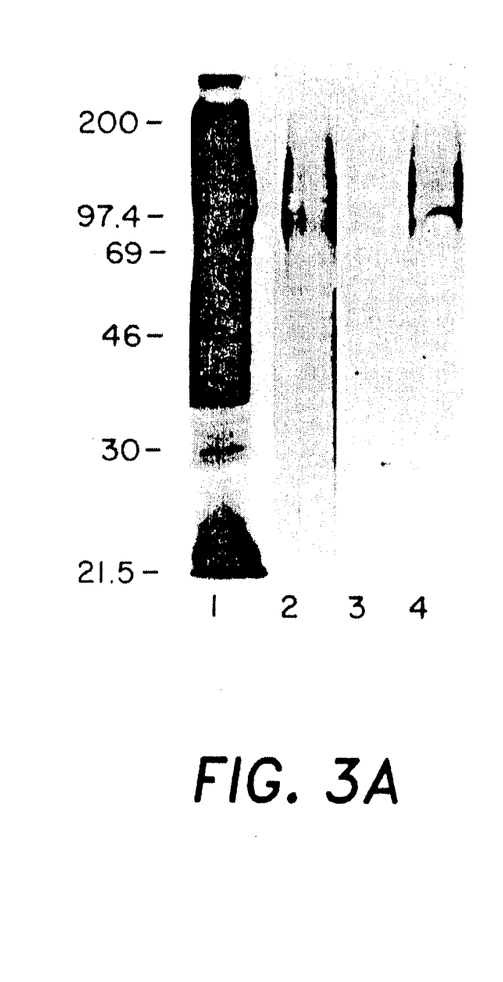

The antigen recognized by monoclonal antibody CC8.6 is a phosphorylated, lipid-containing, glycoconjugate. To determine whether the antigen bound by CC 8.6 was glycosylated, in vivo labeling studies were performed on HM1:IMSS trophozoites using [$^{14}$C]glucose. FIG. 3A shows that monoclonal antibody CC 8.6 immunoprecipitated a species spanning an area of the gel corresponding to molecular weight 75 to 200 kDa, from lysates of trophozoites labeled with [$^{14}$C]glucose (lane 4). No species was immunoprecipitated from labeled trophozoites using the control monoclonal antibody HPCμ2 (lane 3).

Figure 4:
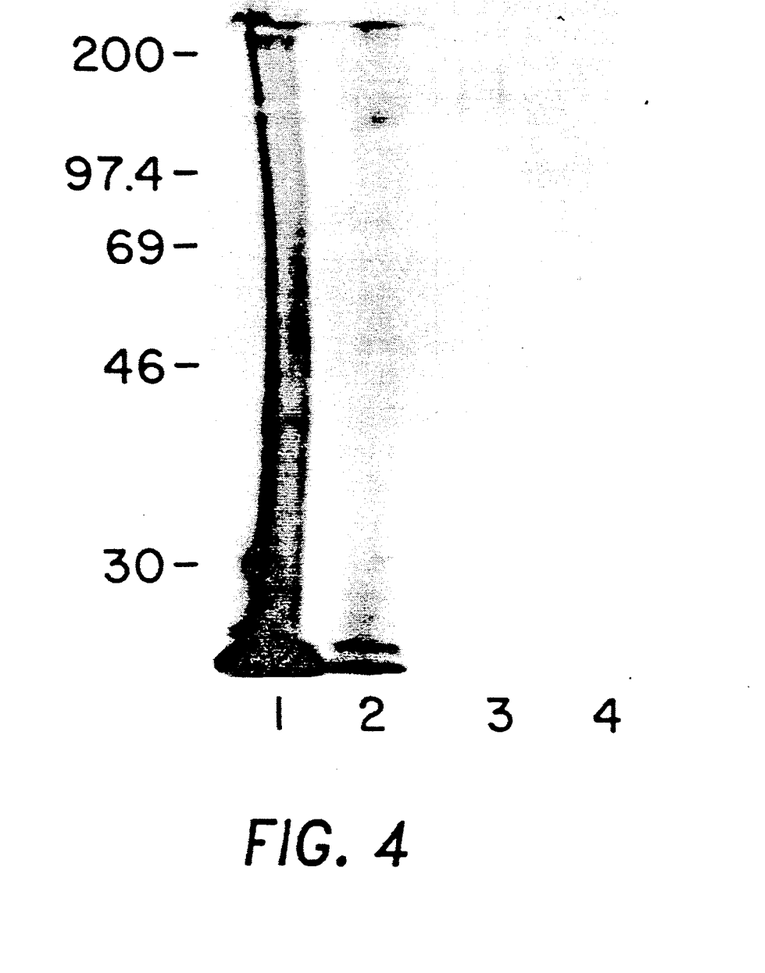

In vivo labeling studies were performed with [$^{3}$H]palmitate to determine whether the antigen recognized by monoclonal antibody CC 8.6 contains lipid. As shown in FIG. 4, monoclonal antibody CC 8.6 immunoprecipitated a species spanning an area of the gel corresponding to protein molecular weights 65 to 200 kDa from the supernatant of lysates of HM1:IMSS trophozoites labeled with [$^{3}$H]palmitate (lane 3). No species was immunoprecipitated by control monoclonal antibody HPCμ2 (lane 4).

Figure 5:
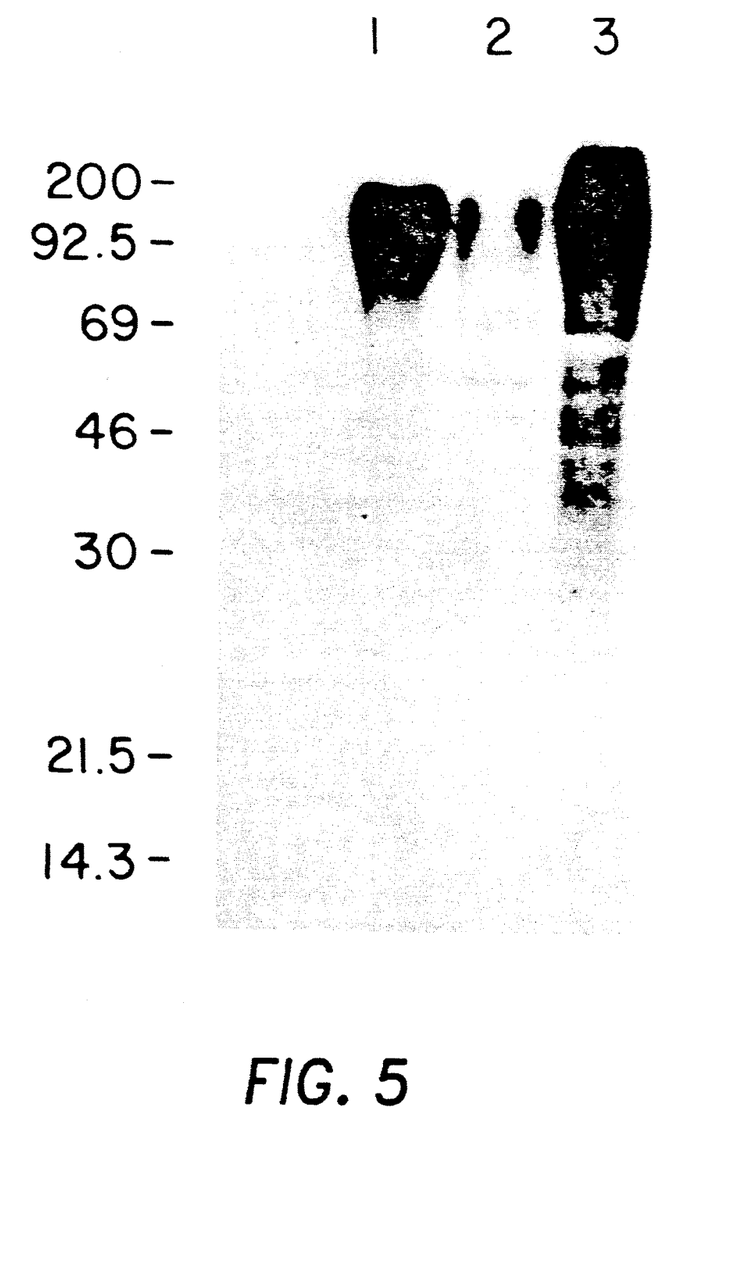

To determine whether the antigen recognized by monoclonal antibody CC 8.6 is phosphorylated, in vivo labeling studies were performed with [$^{32}$P]phosphate. It was found that CC 8.6 immunoprecipitated a species spanning a region of the gel corresponding to protein standard molecular weights 75 to 200 kDa from lysates of HM1:IMSS trophozoites labeled with [$^{32}$P] phosphate (FIG. 5, lane 1). No species was immunoprecipitated by control monoclonal antibody HPCμ2.

In vivo labeling studies with [$^{35}$S]methionine and surface labeling studies using [$^{125}$I]iodine showed that the phosphorylated, lipid-containing, amebic glycoconjugate did not incorporate [$^{35}$S]methionine, and could not be labeled with [$^{125}$I].

Isolation of the amebic glycoconjugate using hydrophobic interaction chromatograohy. In order to purify larger quantities of the amebic glycoconjugate, fractionation was used on an OCTYL-SEPHAROSE column with a protocol identical to that utilized to isolate the lipophosphoglycan molecule of *Leishmania major* [12]. [$^{14}$C]glucose-labeled trophozoites were extracted initially with chloroform:methanol:water (4:8:3 vol/vol/vol) to remove phospholipids. The residue was extracted from delipidated trophozoites with water saturated 1-butanol. Immunoblotting of the chloroform:methanol:water extract, the butanol-saturated water, and the residue of insoluble material, with monoclonal antibody CC 8.6 revealed that the butanol-saturated water fraction contained all of the immunoreactivity, and 85% of the radioactivity incorporated.

Figure 6:
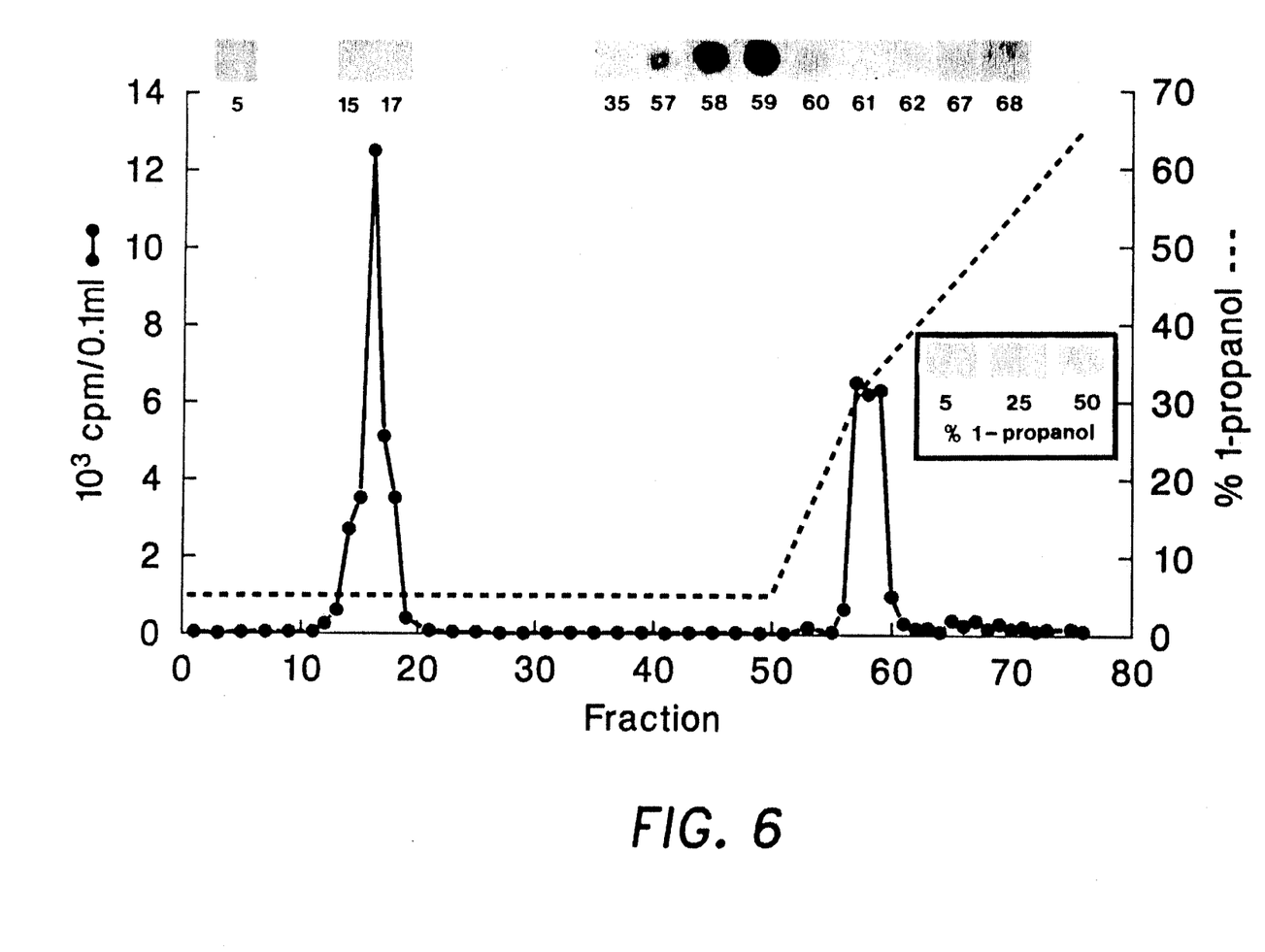
FIG. 6 shows the OCTYL-SEPHAROSE chromatography of the water saturated with 1-butanol extract of delipidated HM1:IMSS trophozoites that had been metabolically labeled with [$^{14}$C]glucose. Elution of the OCTYL-SEPHAROSE column with a linear gradient of 1-propanol in 0.1M TES is shown. Chromatography conditions and analysis of fractions for radioactivity, 1-propanol, and carbohydrate are described below. Immunoblotting of selected fractions with monoclonal antibody CC 8.6 is shown at the top of the figure. No reactivity of any fraction with control monoclonal antibody HPCμ2 was seen. Background non-specific binding to increasing % of 1-propanol is shown in the boxed insert.

The butanol-saturated water extract was lyophilized and subsequently re-extracted with chloroform methanol, which failed to remove immunoreactive material. The dried extract was dissolved in 0.1 M Tes, 5% 1-propanol, and fractionated by hydrophobic interaction chromatography using OCTYL-SEPHAROSE as shown in FIG. 6. Fractions were monitored for radioactivity, and immunoreactivity with monoclonal antibody CC 8.6. Two peaks of radioactivity were observed. The first peak, containing fractions 14-18, failed to bind octyl-Sepharose, and eluted with 0.1 M Tes, 5% 1-propanol. It contained 60% of the radioactivity, but demonstrated no immunoreactivity with the CC 8.6 antibody. The other peak, containing fractions 57–59, was retained on octyl-Sepharose and eluted at 30% 1-propanol. It contained 40% of the radioactivity, and demonstrated immunoreactivity with monoclonal antibody CC 8.6.

Figure 3B:
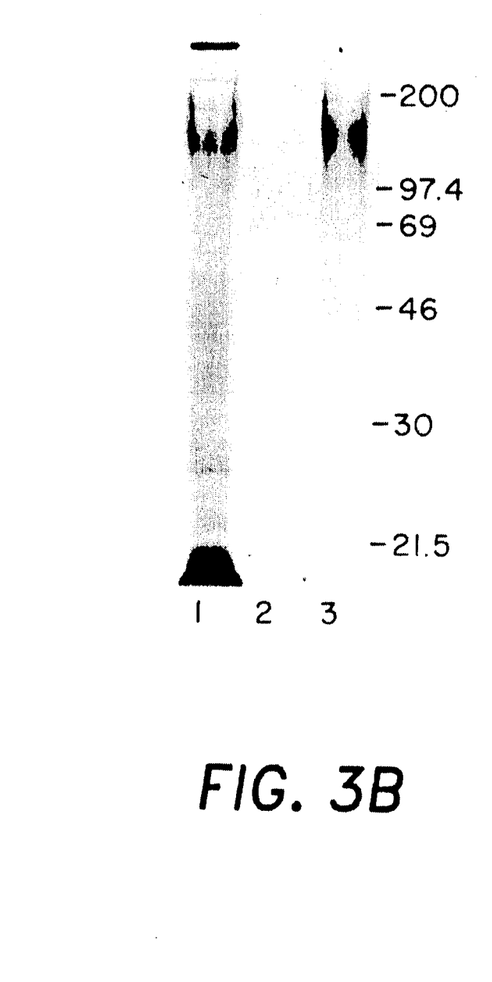

Purification of the amebic glycoconjugate from other labeled carbohydrates was confirmed by SDS-PAGE analysis of the CC 8.6 reactive fraction eluted with 30% 1-propanol (FIG. 3B). Autoradiographic analysis of the CC 8.6 reactive fraction (lane 3) showed that all the radiolabelled material appeared as a diffuse band, spanning the region of the gel corresponding to protein standard molecular mass 75 to 200 kDa; these results were identical to the results seen with immunoprecipitation of [$^{14}$C]glucose-labeled amebic lysates with CC 8.6. (FIG. 3A, lane 4). This band was also present, along with a number of lower molecular weight bands in the starting material (FIG. 3B, lane 1). No band corresponding to amebic glycoconjugate was seen in the non-CC 8.6 reactive [$^{14}$C]glucose-containing fraction 16 (lane 2). This suggests the labeled compound(s) in fraction 16 is probably of very low molecular weight.

To further study the hydrophobic nature of the amebic glycoconjugate the purified [$^{14}$C]glucose-labeled glycoconjugate (fraction 59) was incubated with PI-PLC and binding of the treated glycoconjugate to OCTYL-SEPHAROSE was measured under conditions identical to those described above [12]. Treatment with PI-PLC significantly changed the hydrophobic properties of the glycoconjugate. Of the 80,000 cpm of the PI-PLC treated $^{14}$C]glucose-labeled glycoconjugate reacted with octyl-Sepharose, 65,300 cpm did not bind to octyl-Sepharose, and only 10,500 cpm or 14% of the recovered counts were eluted with 30% 1-propanol.

Figure 7A:
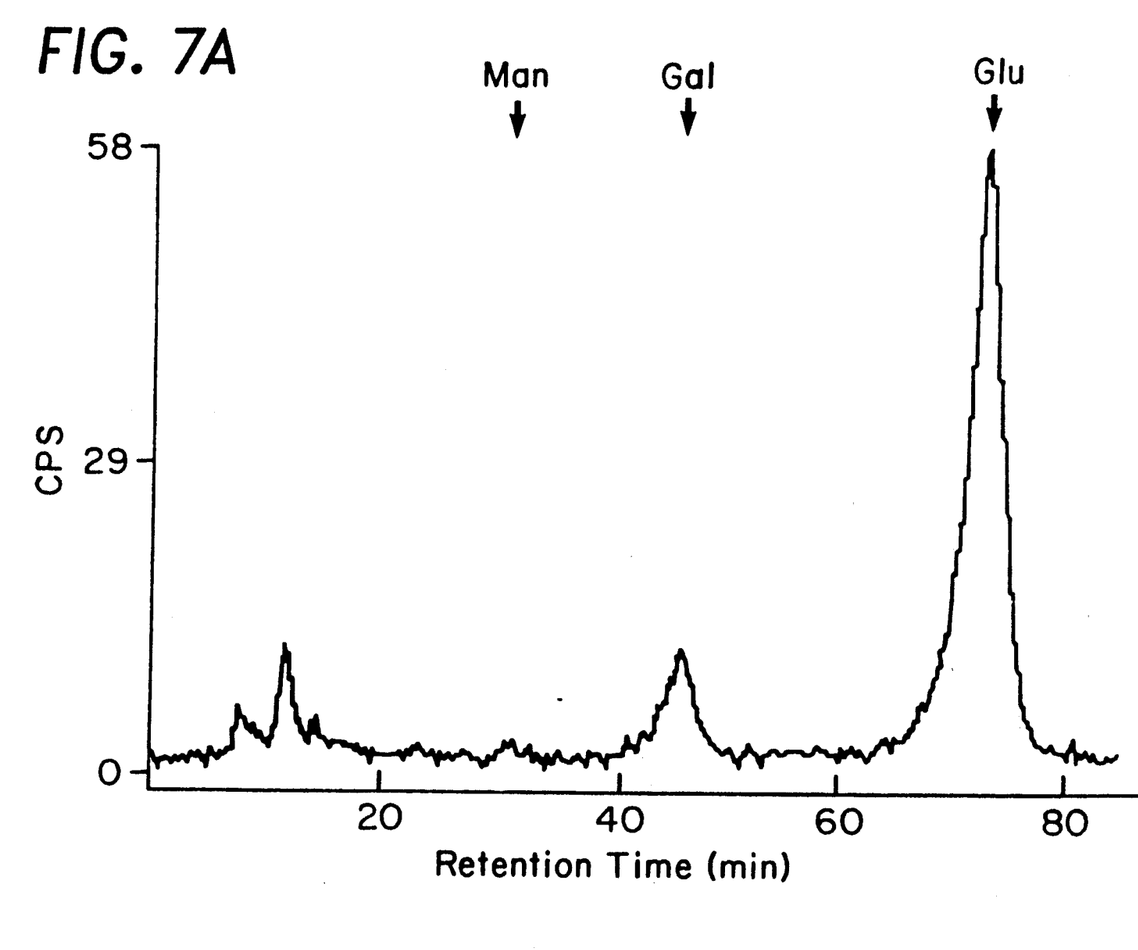
FIG. 7A, non-reduced acid hydrolysate.
Figure 7B:
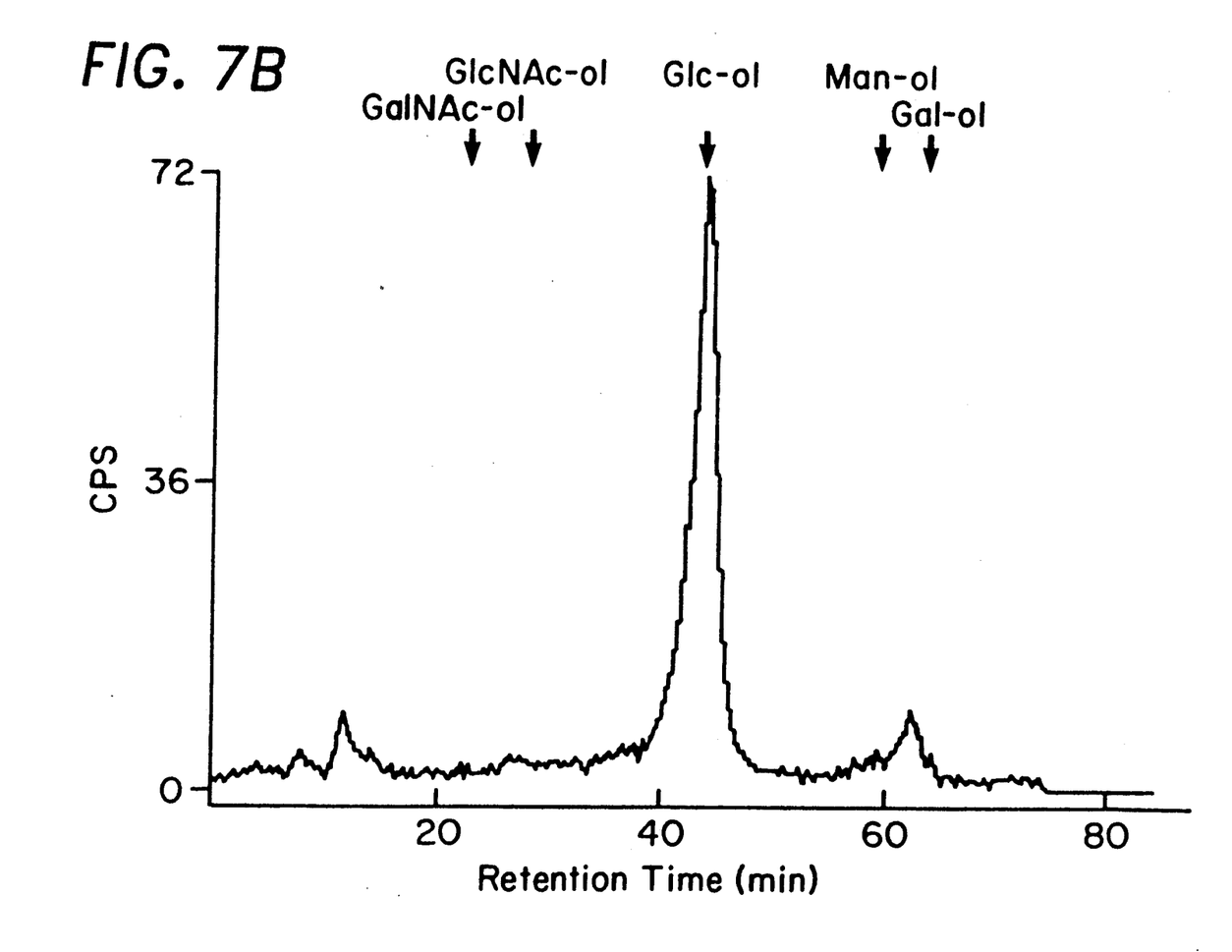
FIG. 7B reduced acid hydrolysate. The locations of the standards are indicated by the arrows.

Identification of the radiolabel in [$^{14}$C]glucose-labeled glycoconjugate. In order to determine the identity of the radiolabel, the [$^{14}$C]glucose-labeled glycoconjugate was subjected to strong acid hydrolysis (2N trifluoracetic acid, 2 hr, 100° C.). The hydrolysate was either analyzed directly by borate anion exchange HPLC to identify labeled aldoses (FIG. 7A), or after reduction with sodium borohydride and re-acetylation to identify labeled alditols (FIG. 7B). Direct analysis of the hydrolysate revealed that approximately 80% of the radioactivity co-eluted with glucose, and 15% of the radioactivity co-eluted with galactose (FIG. 7A). Analysis of the hydrolysate after sodium borohydride reduction revealed that approximately 84% of the radioactivity co-eluted with glucitol, and 8% of the radioactivity co-eluted with galactitol (FIG. 7B). Two small peaks were also observed in FIG. 7A, representing 2% and 5% of the total recovered radioactivity, respectively. The elution times of these peaks were not effected by treatment with sodium borohydride (FIG. 7B), suggesting that these peaks do not represent aldoses.

It was found that none of the radioactivity present in the acid hydrolysate bound to QAE-SEPHAROSE under the conditions described by Varki and Kornfeld [16], suggesting that none of the label is present in phosphorylated sugars.

Figure 8:
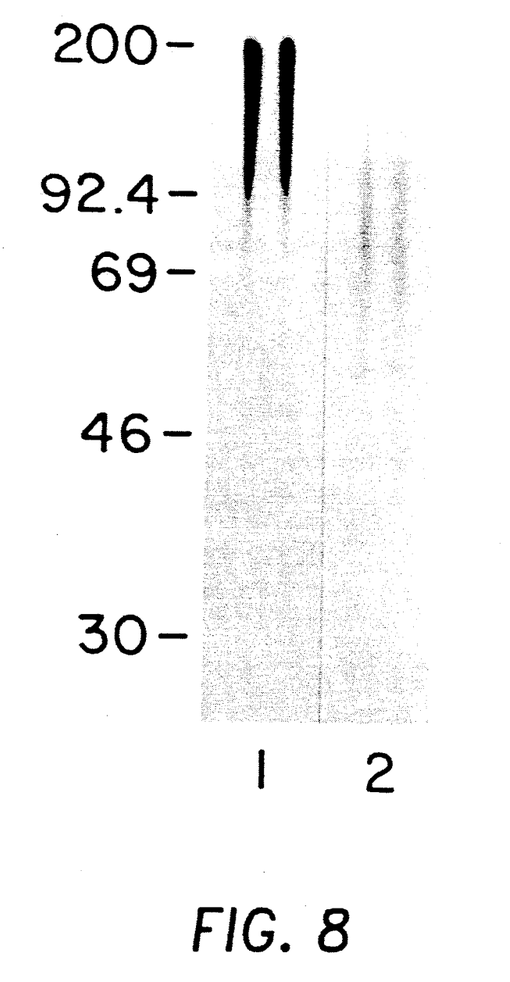
FIG. 8 shows the pronase treatment of [$^{14}$C]glucose-labeled glycoconjugate. Lane 1, glycoconjugate incubated with PBS; lane 2, glycoconjugate incubated with 1 mg ml$^{-1}$ pronase.

Treatment of the [$^{14}$C]glucose labeled glycoconjugate with pronase. The OCTYL-SEPHAROSE purified [$^{14}$C]glucose-labeled glycoconjugate was subjected to digestion with pronase. As shown in FIG. 8, after pronase treatment there was some loss of labeled material and a shift in the migration pattern of the glycoconjugate in SDS-PAGE consistent with the presence of a peptide component in the glycoconjugate. 100 µg of bovine serum albumin was completely digested by 1 mg/ml pronase under similar conditions. Reactivity of the glycoconjugate with monoclonal antibody CC 8.6 (as measured by ELISA) was not altered by pronase treatment.

TABLE I

Inhibition of HM1:IMSS trophozoite adhesion to 1021 Chinese Hamster Ovary cells and HM1:IMSS-mediated cytotolysis of 1021 Chinese Hamster Ovary cells by monoclonal antibody CC 8.6.

|  | CC 8.6 | HPC µ2 |  |
|---|---|---|---|
| % control adhesion to 1021 cells[a] | 2 ± 2 | 81 ± 4 | $p < 0.005$ |
| % control cytolysis of 1021 cells[b] | 45 ± 11 | 83 ± 5 | $p < 0.025$ |

[a]The adhesion % was defined as [cpm in sample/cpm in media control] × 100. Values are the averages from 3 experiments. Each sample was run in quadruplicate. Ascites of monoclonal CC 8.6 and the control monoclonal antibody HPC µ2 were used at a 1:500 dilution.
[b]The % cytotoxicity was defined as [cpm released in sample/cpm released by HM1:IMSS without inhibitors × 100. Values are the averages from three experiments. Each sample was run in quadruplicate. Ascites of monoclonal antibody CC 8.6 and the control monoclonal antibody HPC µ2 were used at a 1:10 dilution.

Various other examples will be apparent to the person skilled in the art after reading the present disclosure without departing from the spirit and scope of the invention. It is intended that all such other examples be included within the scope of the appended claims.

References to conventional, published methods cited in brackets herein are appended as follows:

1 Ravdin, J. I., Croft, B. V. and Guerrant, R. L. (1980) Cryptopathogenic mechanisms of Entamoeba histolytica. J. Exp. Med 152, 377–390.

2 Diamond, L. S., Harlow, D. and Cunnick, C. C. (1978) A new medium for the axenic cultivation of Entamoeba histolytica and other Entamoeba. Trans. R. Soc. Trop Med. Hyg. 4, 431–432.

3 Briles, E. B., Li, E, and Kornfeld, E. (1977) Isolation of wheat germ agglutinin-resistant clones of Chinese hamster ovary cells deficient in membrane sialic acid and galactose. J. Biol. Chem. 252, 1107–11116.

4 Kohler, G. and Milstein. C. (1976) Derivation of specific antibody-producing tissu Ⓡculture and tumor lines by cell fusion, Eur. J. Immunol. 6, 511–515.

5 Stanley, S. L., Li, E. and Davie, J. M. (1988) Antigen induced rheumatoid factors: characteristics of monoclonal rheumatoid factors produced after protein and carbohydrate immunization. Mol. Immunol. 25, 285–294.

6 Avrameas, S. (1969) Coupling of enzymes to proteins with glutaraldehyde. Use of the conjugates for the detection of antigens and antibodies. Immunochemistry 6, 43–49.

7 Li. E., Becker, A. and Stanley Jr., S.L. (1988) Use of Chinese hamster ovary cells with altered glycosylation patterns to define the carbohydrate specificity of Entamoeba histolytica adhesion. J. Exp. Med. 167, 1725–1730.

8 Li, E., Becker, A. and Stanley Jr., S. L. (1989) Chinese hamster ovary cells deficient in N-acetylglucosaminyl-transferase I activity are resistant to Entamoeba histolytica-mediated cytotoxicity. Infect. Immun. 57, 8–12.

9 Stanley Jr., S. L., Becker, A. Kunz-Jenkins. C., Foster. L. and Li, E. (1990) Cloning and expression of a membrane antigen of Entamoeba histolytica possessing multiple tandem repeats. Proc. Natl. Acad. Sci. USA 87, 4976–4980.

10 Svennerholm. L. and Freedman. p. (1980) A procedure for the quantitative isolation of brain gangliosides. Biochim. Biophys. Acta 617, 97–109.

11 Korn, E. D., Dearborn, D. G. and Wright, P. L. (1974) Lipophosphonoglycan of the plasma membrane of *Acanthamoeba castellanii*. J. Biol. Chem. 249, 3335–3341.

12 McConville, M. J., Bacic, A., Mitchell, G. F. and Handman, E. (1987) Lipophosphoglycan of *Leishmania major* that vaccinates against cutaneous leishmaniasis contains an alkyglycerophosphoinositol lipid anchor. Proc. Natl. Acad. Sci. USA 84, 8941–8945.

13 Henner, D. J., Yang, M., Chen, E., Hellmiss, R., Rodriquez, H. and Low, M. (1988) Sequence of the *Bacillus thuringiensis* phosphatidylinositol specific phospholipase C Nucleic Acids Res. 16, 10383–1038.

14 Baar, J, and Nordin, P. (1980) Microdetermination of neutral and amino sugars found in glycoproteins. Anal. Biochem, 108, 313-319.

15 Chandrashekar, R., Ogunrinade, A. F., Alvarez, R. M., Kale, O. O. and Weil, G. (1990) Circulating immune complex-associated parasite antigens in human onchocerciasis. J. Infect. Dis. 162, 1159-1164.

16 Varki, A. and Kornfeld, S. (1980) Structural studies of phosphorylated high mannose-type oligosaccharides. J. Biol. Chem. 255, 10847-10858.

What is claimed is:

1. Monoclonal antibody having the identifying antigenic binding characteristics of CC 8.6, ATCC HB 11104.

2. A purified amebic antigen isolated from lysates of *Entamoeba histolytica trophozoites which is phosphorylated, lipid-containing, glycosylated, migrates as a polydisperse band on SDS-PAGE between about* 65 to 200 kDa and is specifically antigenically recognized by binding of said antigen to monoclonal antibody CC 8.6, ATCC HB 11104.

3. A method for the detection of the amebic antigen of claim 2 comprising contacting an aqueous solution of *Entamoeba histolytica trophozoites with monoclonal antibody CC* 8.6, ATCC HB 11104, and measuring the antibody-antigen reaction.

* * * * *